United States Patent
Boone et al.

(10) Patent No.: US 7,311,657 B2
(45) Date of Patent: Dec. 25, 2007

(54) PATIENT-SUPPORT DEVICE AND DOCKING CART COMBINATION

(75) Inventors: Otho N. Boone, Ambler, PA (US); Ian McDermott, Lincoln University, PA (US); John H. Richards, Warrington, PA (US); Nancy St. Clair, Malvern, PA (US)

(73) Assignee: Draeger Medical Systems, Inc., Telford, PA (US)

( * ) Notice: Subject to any disclaimer, the term of this patent is extended or adjusted under 35 U.S.C. 154(b) by 484 days.

(21) Appl. No.: 10/490,825

(22) PCT Filed: Oct. 3, 2002

(86) PCT No.: PCT/US02/31636

§ 371 (c)(1),
(2), (4) Date: Mar. 25, 2004

(87) PCT Pub. No.: WO03/030798

PCT Pub. Date: Apr. 17, 2003

(65) Prior Publication Data

US 2004/0236175 A1    Nov. 25, 2004

Related U.S. Application Data

(60) Provisional application No. 60/327,496, filed on Oct. 5, 2001.

(51) Int. Cl.
*A61G 11/00* (2006.01)

(52) U.S. Cl. ............................. 600/22; 312/209; 5/603

(58) Field of Classification Search ............ 600/21–22; 5/1, 81.1, 86.1, 95, 503.1, 504.1, 505.1, 506.1, 5/507.1, 509.1, 510–513, 600, 603, 613, 5/616, 620, 658–663; 312/209, 298

See application file for complete search history.

(56) References Cited

U.S. PATENT DOCUMENTS

| | | | | |
|---|---|---|---|---|
| 2,459,301 | A | * | 1/1949 | Adams ...................... 312/328 |
| 2,663,608 | A | * | 12/1953 | Schauer ..................... 312/326 |
| 3,470,866 | A | | 10/1969 | Gittelson |
| 5,117,521 | A | * | 6/1992 | Foster et al. .................. 5/510 |
| 5,308,310 | A | | 5/1994 | Roff et al. |
| 5,335,651 | A | * | 8/1994 | Foster et al. .......... 128/202.13 |
| 5,453,077 | A | | 9/1995 | Donnelly et al. |
| 5,745,366 | A | * | 4/1998 | Higham et al. ............. 700/242 |
| 5,759,149 | A | | 6/1998 | Goldberg et al. |
| 5,817,002 | A | | 10/1998 | Donnelly et al. |

(Continued)

FOREIGN PATENT DOCUMENTS

DE    73 34 435.1    1/1974

(Continued)

*Primary Examiner*—John P. Lacyk
(74) *Attorney, Agent, or Firm*—Caesar, Rivise, Bernstein, Cohen & Pokotilow, Ltd.

(57) ABSTRACT

A combination comprises a patient-support device and one or more carts that dock to the patient-support device. Some of the disclosed carts that dock to the patient-support device have pivotable storage bins. Some of the disclosed carts have equipment-carrying surfaces. Some of the disclosed carts have work surfaces or trays that move between storage and use positions. One of the disclosed carts has a storage module that transfers from a frame of the cart to a base of the patient-support device.

29 Claims, 6 Drawing Sheets

U.S. PATENT DOCUMENTS

| | | |
|---|---|---|
| 5,817,003 A | 10/1998 | Moll et al. |
| 5,898,961 A | 5/1999 | Ambach et al. |
| 5,971,913 A | 10/1999 | Newkirk et al. |
| 5,971,914 A | 10/1999 | Donnelly et al. |
| 6,022,310 A | 2/2000 | Goldberg et al. |
| 6,024,694 A | 2/2000 | Goldberg et al. |
| 6,036,634 A | 3/2000 | Goldberg et al. |
| 6,049,924 A | 4/2000 | Prows et al. |
| 6,071,228 A | 6/2000 | Speraw et al. |
| 6,073,285 A | 6/2000 | Ambach et al. |
| 6,210,320 B1 | 4/2001 | Rogone et al. |
| 6,270,452 B1 | 8/2001 | Donnelly et al. |
| 6,296,606 B1 | 10/2001 | Goldberg et al. |
| 6,345,402 B1 | 2/2002 | Prows et al. |
| 6,367,476 B1 | 4/2002 | Conn |
| 6,375,017 B1 | 4/2002 | Schattner et al. |
| 6,481,739 B1 | 11/2002 | Newkirk |
| 6,483,080 B2 | 11/2002 | Richards et al. |
| 6,540,660 B1 | 4/2003 | Speraw et al. |
| 6,543,369 B1 * | 4/2003 | Swensson et al. ............ 108/49 |
| 6,709,384 B1 | 3/2004 | Donnelly et al. |
| 2001/0035702 A1 | 11/2001 | Murphy et al. |
| 2002/0087045 A1 * | 7/2002 | Chamorro-Perez et al. ... 600/21 |
| 2002/0143232 A1 | 10/2002 | Richards et al. |
| 2002/0196141 A1 | 12/2002 | Boone et al. |

FOREIGN PATENT DOCUMENTS

| | | |
|---|---|---|
| DE | 24 33 882 | 2/1976 |
| DE | 32 05 097 A1 | 10/1982 |
| DE | 39 15 882 A1 | 11/1990 |
| DE | 42 28 873 C1 | 10/1993 |
| WO | WO 99/12511 A1 | 3/1999 |
| WO | WO 00/69387 A1 | 11/2000 |

* cited by examiner

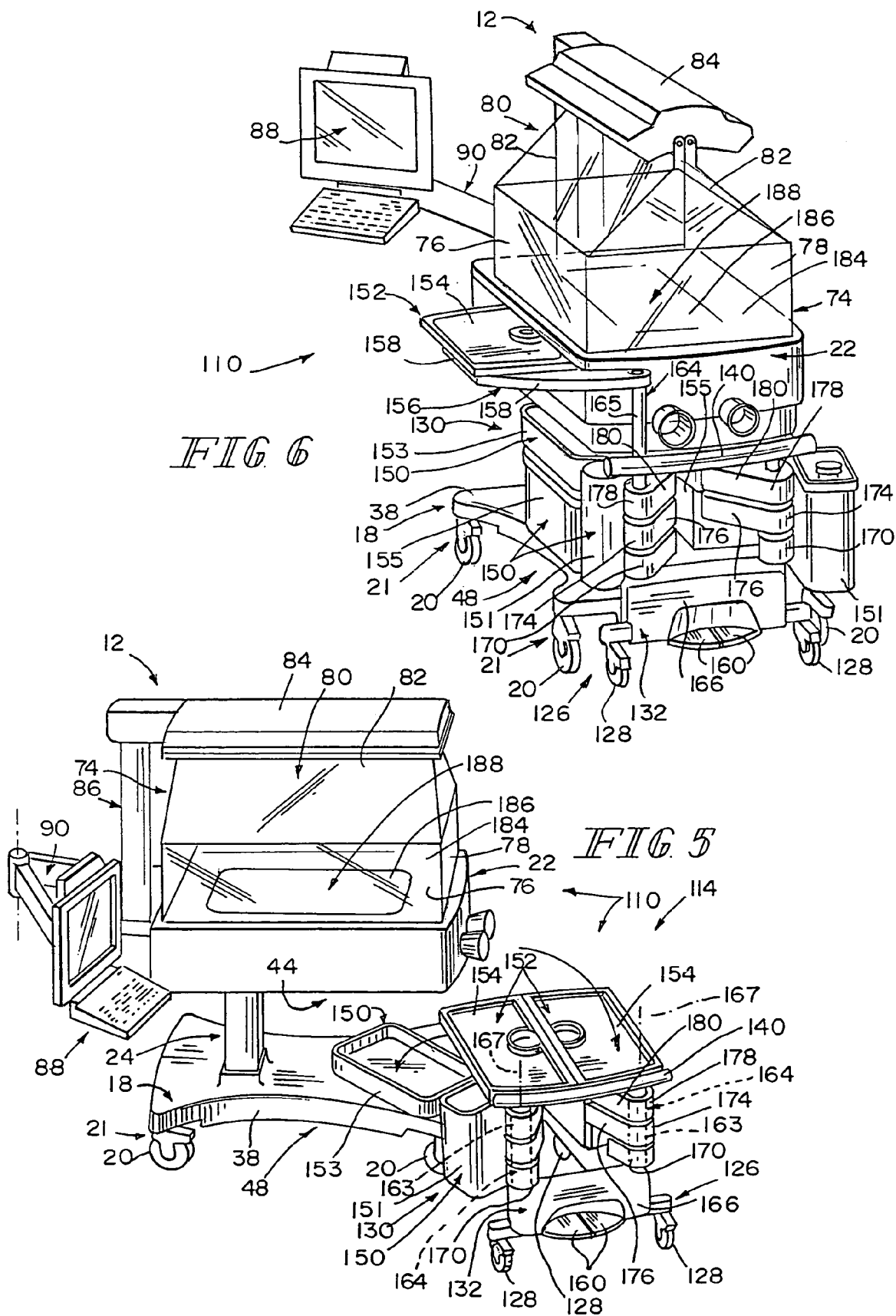

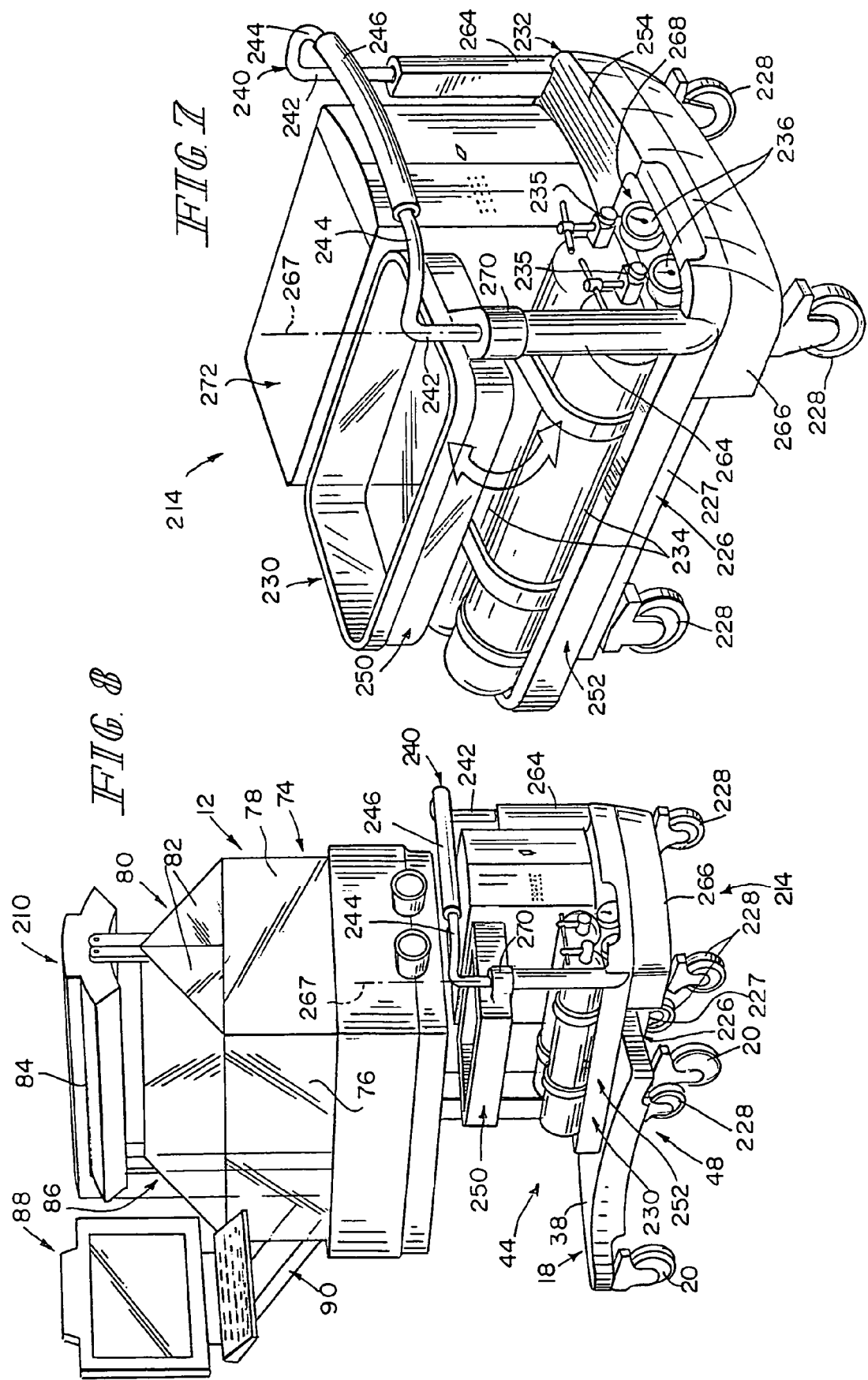

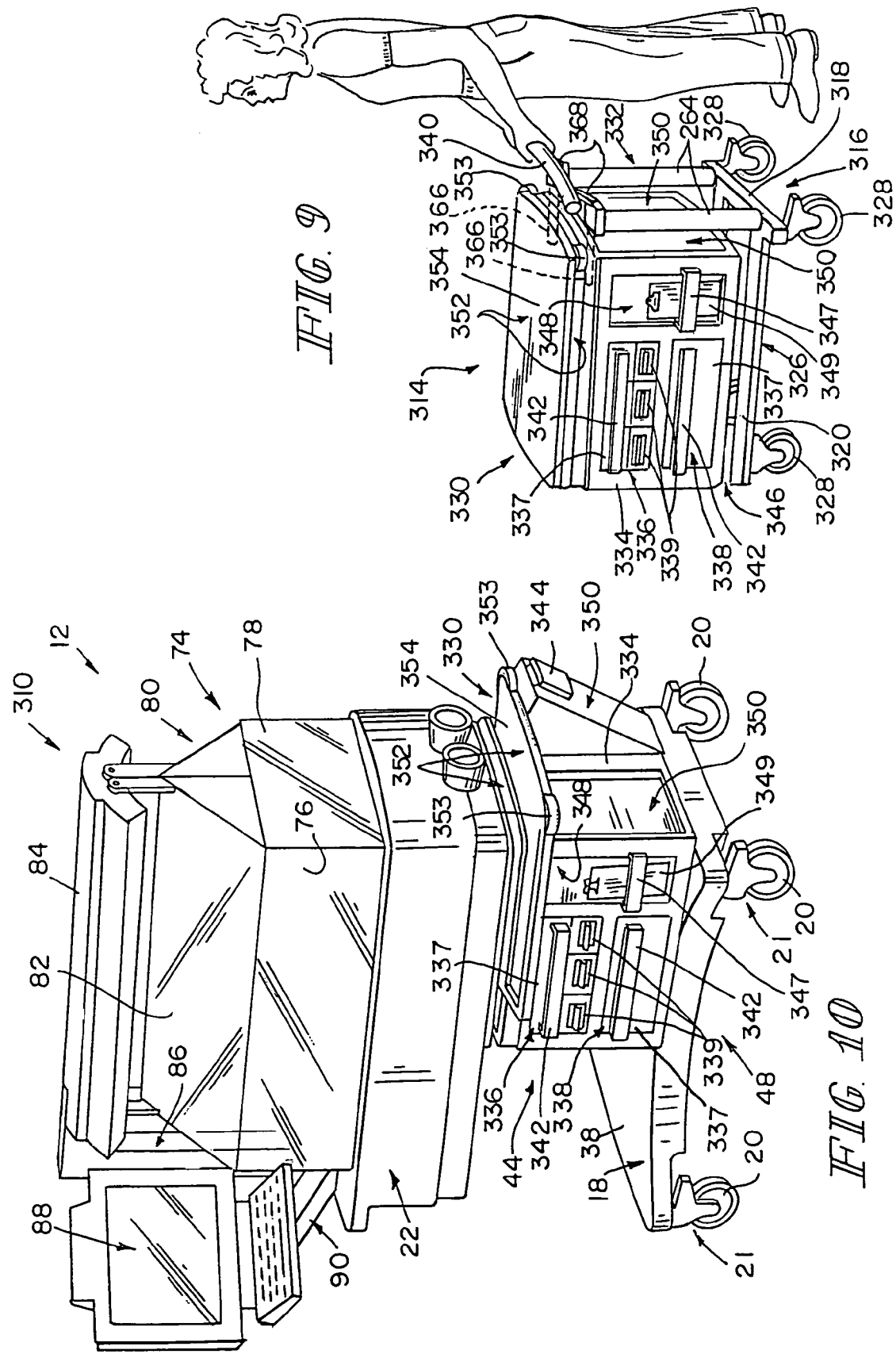

PATIENT-SUPPORT DEVICE AND DOCKING CART COMBINATION

CROSS-REFERENCE TO RELATED APPLICATIONS

This application is a U.S. national counterpart application of international application Ser. No. PCT/US02/31636 filed Oct. 3, 2002, which claims the benefit of U.S. provisional application Ser. No. 60/327,496 filed Oct. 5, 2001.

BACKGROUND OF THE INVENTION

The present disclosure relates to patient-support devices, such as infant thermal support devices, that support patients during their stays in hospitals and to carts that dock to patient-support devices. More particularly, the present disclosure relates to carts that carry supplies and/or equipment and that dock to mobile patient-support devices to be transported with the patient-support devices.

Mobile patient-support devices on which patients lie or sit during their stays in hospitals are known. Such devices include, for example, hospital beds, stretchers, and, in the case of premature infants, infant thermal support devices, such as incubators, radiant warmers, and combination incubator/radiant warmer devices. A variety of medical equipment and supplies are typically needed to care for a patient in a hospital. Sometimes the equipment and supplies used to care for patients are carried by carts that are able to dock to the patient-support devices on which patients rest.

SUMMARY OF THE INVENTION

According to this disclosure, a combination comprises a patient-support device and one or more carts that dock to the patient-support device. An illustrative patient-support device has a base, a set of wheels coupled to the base, and a patient-support platform supported above the base such that a first space for receiving a portion of a cart is defined between the base and the patient-support platform. In illustrative embodiments, a cart has a base, a set of wheels coupled to the base, and a structure for carrying supplies and/or equipment supported above the base such that a second space is defined between the structure and the base of the cart. When the illustrative cart is docked to the illustrative patient-support device, at least a portion of the structure of the cart is situated in the first space of the patient-support device and at least a portion of the base of the patient-support device is situated in the second space of the cart.

One illustrative cart has a base, a set of wheels coupled to the base, a post coupled to the base, and at least one bin coupled to the post for pivoting movement relative to the post. Another illustrative cart has a tray or shelf that is movable between a storage position received in the space beneath the patient-support platform and a use position situated alongside the patient-support platform. A further illustrative cart has a base, a set of wheels coupled to the base, and an equipment-support shelf that is supported above the base and that has an upper surface configured with at least one recess adapted to receive at least a portion of a piece of medical equipment. Yet another illustrative cart has a frame and a storage module that detaches from the frame and that couples to the patient-support device beneath the patient-support platform and above the base.

In some illustrative embodiments in which a cart docks to a patient-support device, the patient-support device comprises a base having a base frame and a shroud covering at least a portion of the base frame. In such embodiments, a docking mechanism has a first docking portion coupled to the base frame beneath the shroud and a second docking portion coupled to a base of the cart. To dock the cart to the patient-support device, at least a portion of the base of the cart is moved underneath the base of the patient-support device so that the second docking portion engages the first docking portion to couple the cart and patient-support devices together. In such embodiments, when the cart is docked to the patient-support device, the shroud shields the docking mechanism from view. In other embodiments, the shroud is omitted or is otherwise configured so that the docking mechanism is not shielded from view.

Additional features will become apparent to those skilled in the art upon consideration of the following detailed description of illustrative embodiments exemplifying the best mode of carrying out the patient-support device and docking cart combination as presently perceived.

BRIEF DESCRIPTION OF THE DRAWINGS

The detailed description particularly refers to the accompanying figures, in which:

FIG. 5 is a perspective view of a combination of the patient-support device of FIGS. 1-3 and of a first alternative cart that is releasably dockable to the patient-support device showing the first alternative cart undocked from the patient-support device, the first alternative cart having a pair of work surfaces overlying a plurality of storage bins, and two of the storage bins pivoted part way out from underneath one of the work surfaces;

FIG. 6 is a perspective view of the combination of FIG. 5 showing the first alternative cart docked to the patient-support device, one of the work surfaces moved out from underneath the patient-support platform and raised to a position alongside the patient-support platform, and one of the storage bins pivoted to a position out from underneath the patient-support platform;

FIG. 7 is a perspective view of a second alternative cart showing an equipment-support shelf of the cart supporting a pair of gas tanks and a power unit and showing a storage bin of the cart mounted to a post of the cart for pivoting movement in the direction of the double arrow about a vertical axis defined by the post;

FIG. 8 is a perspective view of the second alternative cart of FIG. 7 docked to the patient-support device of FIGS. 1-6 showing a majority of the shelf, the equipment on the shelf, and the storage bin situated in the space defined between the base and the patient-support platform of the patient-support device;

FIG. 9 is a perspective view of a third alternative cart showing the cart having a frame, a set of casters coupled to horizontal frame members of the frame, a push handle coupled to vertical frame members of the frame, and a storage module supported by the vertical frame members so that a base-receiving space is defined between the storage module and the horizontal frame members; and FIG. 10 is a perspective view of a combination of the patient-support device of FIGS. 1-6 and 8 and the storage module of the cart of FIG. 9 showing the storage module received in the space defined between the base and the patient-support platform of the patient-support device after the frame of the cart of FIG. 9 has been decoupled from the storage module.

DETAILED DESCRIPTION OF THE DRAWINGS

Figure 1:
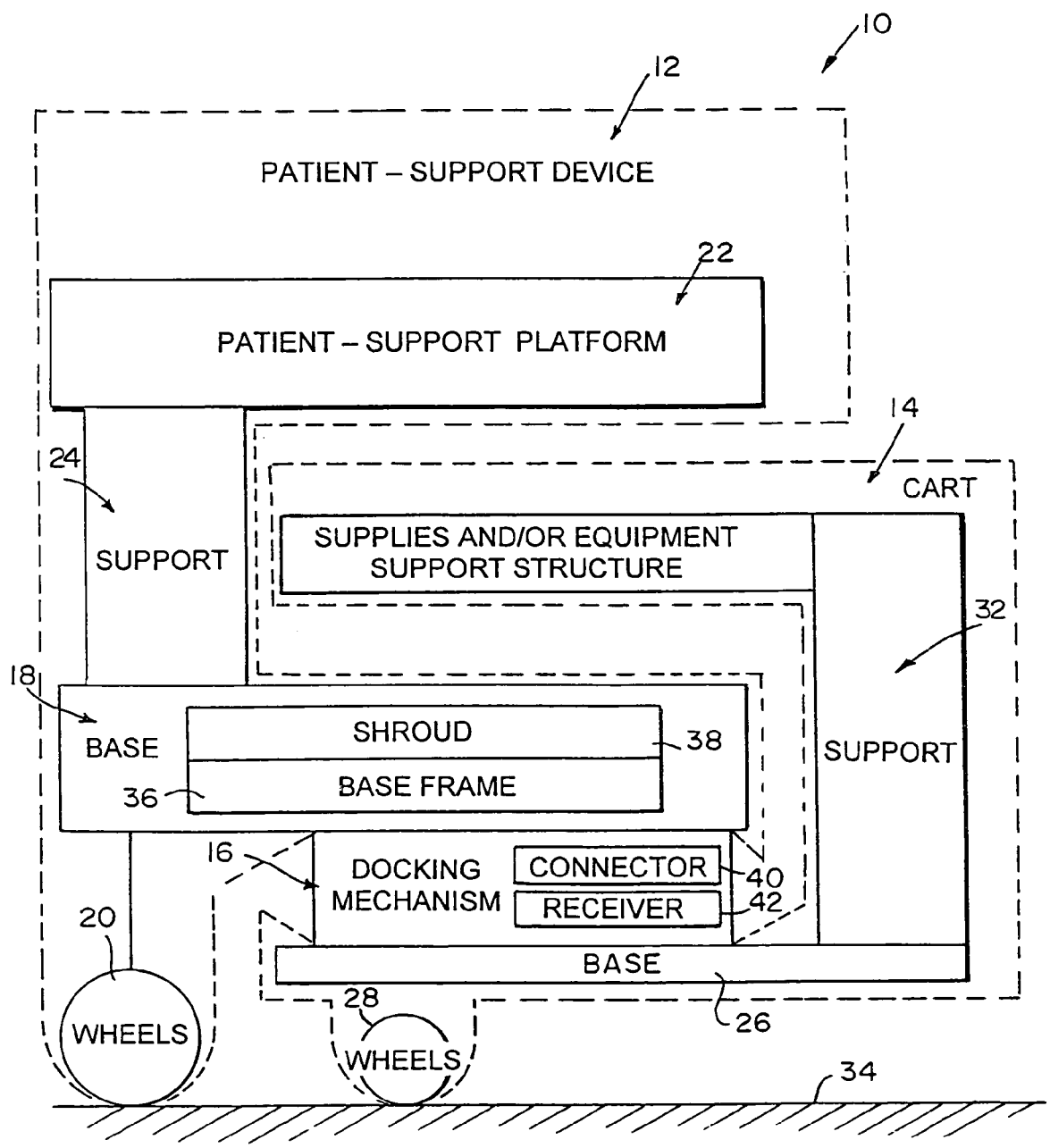
FIG. 1 is diagrammatic view showing a combination having a patient-support device, a cart, and a docking mechanism that releasably couples the cart to the patient-support device.
Figure 2:
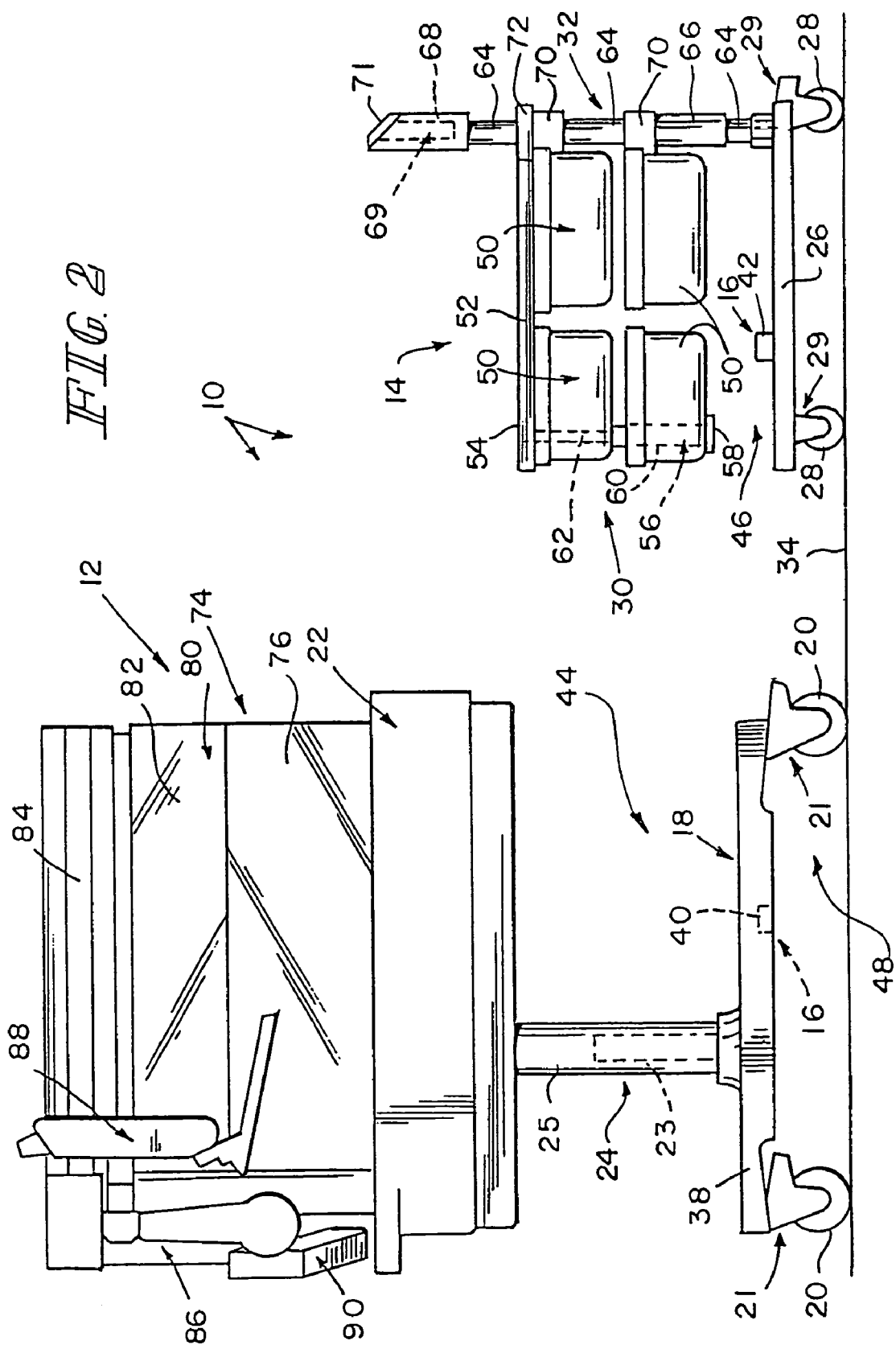
FIG. 2 is a side elevation view of the combination of FIG. 1 showing the cart on the right-hand side of the FIG. separated from the patient-support device on the left-hand side of the FIG.
Figure 3:
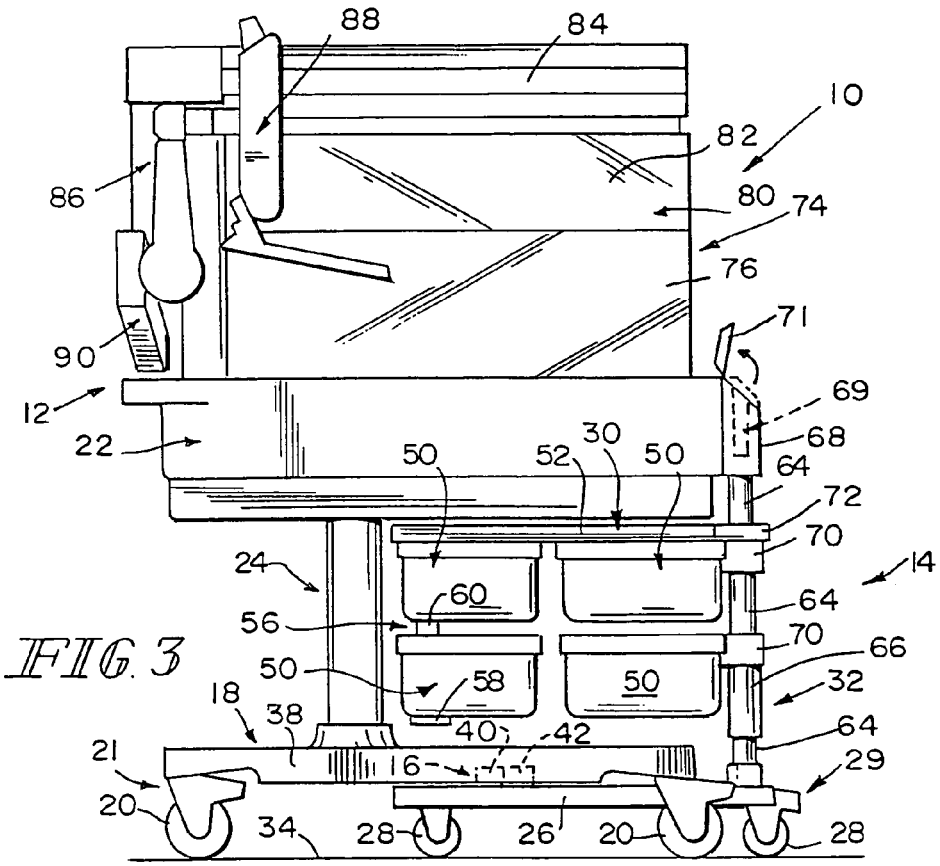
FIG. 3 is a side elevation view of the combination of FIG. 2 showing the cart docked to the patient-support device so that a base of the cart is received, in part, beneath a base of the patient-support device and so that a supply-storage structure of the cart is received, in part, in a space defined between the base of the patient-support device and a patient-support platform of the patient-support device.

According to this disclosure, a combination 10 comprises a patient-support apparatus or device 12, a cart 14, and a docking mechanism 16 that releasably couples cart 14 to device 12 as shown diagrammatically in FIG. 1. Device 12 has a base 18, a set of wheels 20 coupled to base 18, a patient-support platform 22, and a support 24 that supports platform 22 above base 18 as shown in FIGS. 1-3. Cart 14 has a base 26, a set of wheels 28 coupled to base 26, a structure 30 for supporting supplies and/or equipment, and a support 32 that supports structure 30 above base 26 as shown in FIGS. 1-3.

Wheels 20, 28 engage a floor or ground surface 34 over which device 12 and cart 14 are transported as a unit when cart 14 is docked to device 12 and over which device 12 and cart 14 are transported independently when cart 14 is undocked from device 12. Illustrative wheels 20, 28 are part of casters 21, 29, respectively, and therefore, are able to swivel about respective vertical axes in a manner well-known to those skilled in the art. In alternative embodiments, some or all of wheels 20, 28 are not able to swivel, but rather are either rotatable about a fixed horizontal axis or are steerable via appropriate steering mechanisms (not shown). As used in this disclosure, including in the claims, the term "wheel(s)" is intended to cover all types of structures, assemblies, or elements, including, for example, tracks, belts, rollers, balls, and the like, that support a patient-support device or a cart on a floor and that provide for the movement of the patient-support device or cart along the floor.

Figure 4:
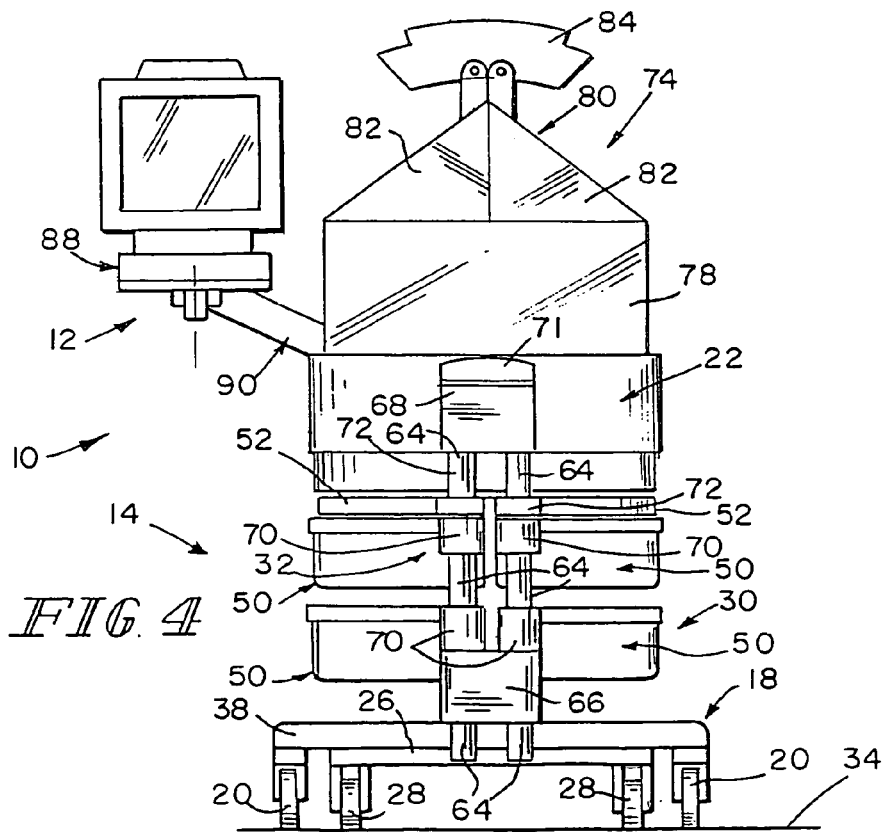
FIG. 4 is an end elevation of the combination of FIG. 3 showing a pair of casters of the cart being spaced apart by a distance less than a distance that a pair of casters of the patient-support device are spaced apart and showing the supply-storage structure of the cart having sides that are generally in alignment with sides of the patient-support platform.

Device 12 is configured so that a first space 44 is defined between base 18 and platform 22 as shown in FIG. 2. Cart 14 is configured so that a second space 46 is defined between base 26 and structure 30 as also shown in FIG. 2. A third space 48 is defined beneath base 18 of device 12. When cart 14 is docked to device 12, as shown in FIGS. 3 and 4, a portion of structure 30 of cart 14 is received in space 44 of device 12, a portion of base 18 of device 12 is received in space 46 of cart 14, and a portion of base 26 of cart 14 is received in space 48 beneath base 18 of device 12. Device 12 and cart 14 are transportable as a unit after cart 14 docks to device 12.

Base 18 of illustrative device 12 has a base frame 36 and a shroud 38 that covers frame 36 as shown diagrammatically in FIG. 1. Docking mechanism 16 includes a first portion or connector 40 and a second portion or receiver 42 that receives connector 40 when cart 14 is docked to device 12. One of portions 40, 42 is coupled to or formed in base frame 36 and the other of portions 40, 42 is coupled to or formed in base 26. Illustratively, connector 40 is associated with base 18 of device 12 and receiver 42 is associated with base 26 of cart 14. However, in alternative embodiments, connector 40 is associated with base 26 of cart 14 and receiver 42 is associated with base 18 of device 12. All types of docking mechanisms having first portions and second portions that releasably couple together are considered to be within the scope of this disclosure for coupling cart 14 to device 12. Such docking mechanisms include, for example, the devices that are shown and described in U.S. Pat. Nos. 6,073,285 and 5,898,961 and in U.S. patent application Ser. No. 09/310,250; each of which is hereby incorporated by reference herein.

When cart 14 is docked to device 12, all portions of docking mechanism 16 are located underneath shroud 38 so as to be generally hidden from view as shown, for example, in FIG. 3. In alternative embodiments, shroud 38 is omitted or is otherwise configured, such as by covering only part of base frame 36, so that some or all of docking mechanism 16 is not hidden from view. Either docking mechanism 16 and/or bases 18, 26 are configured so that, when cart 14 is docked to device 12, base 26 of cart 14 remains in a fixed orientation relative to base 18. A suitable release mechanism (not shown), such as a hand-operated release mechanism or a foot-operated release mechanism, is provided on either cart 14 or device 12 to release docking mechanism 16 to permit separation of portions 40, 42, thereby permitting decoupling of cart 14 from device 12.

Structure 30 of illustrative cart 14 comprises a plurality of bins 50, shown in FIGS. 2-4, in which supplies, waste, or equipment may be placed by caregivers, if desired. Structure 30 further comprises a pair of shelves or trays 52 above bins 50. Each of bins 50 and trays 52 are independently movable between respective storage positions, situated above base 26 of cart 14, and use positions, situated outwardly from the storage positions. Bins 50 and trays 52 are situated beneath platform 22 in space 44 when cart 14 is docked to device 12 and bins 50 and trays 52 are in the respective storage positions. Bins 50 and strays 52 are situated at least partially out from underneath platform 22 and at least partially outside of space 44, when cart 14 is docked to device 12 and bins and trays 52 are in the respective use positions.

Each of trays 52 has an upwardly facing work surface 54 as shown in FIG. 2. When either of trays 52 is in the use position, caregivers may use the associated work surface 54 for a variety of purposes, such as to support supplies and/or equipment or to provide a surface on which to place paper, notepads, charts, and the like. Structure 30 also has a pair of posts 56, each of which hangs or extends vertically downwardly from a respective tray 52 as shown in FIG. 2. Two bins 50 are coupled to each post 56 for pivoting movement about vertical axes defined by the respective posts 56. Each of the bins 50 coupled to posts 56 is movable independently of the other bins 50 between a storage position situated underneath the associated tray 52 and a use position situated at least partly out from underneath the associated tray 52 so that items can be placed in or removed from open tops of bins 50.

Each post 56 has a lower disk 58, an intermediate cylindrical portion 60 extending upwardly from disk 58, and an upper cylindrical portion 62 extending upwardly from portion 60 as shown in FIG. 2. A first diameter of disk 58 is larger than a second diameter of portion 60 and a third diameter of portion 62 is smaller than the second diameter of portion 60. The lowermost pair of bins 50 coupled to posts 56 each have bottom walls that are formed to include openings which receive respective portions 60 of posts 56 with a minimal amount of clearance therebetween. Similarly, the uppermost pair of bins 50 coupled to posts 56 each have bottom walls that are formed to include openings which receive respective portions 60 of posts 56 with a minimal amount of clearance therebetween. Thus, as bins 50 pivot about posts 56, a rotative bearing interface is provided between the edges that define the openings in the bottom wall of the bins 50 coupled to posts 56 and the outer cylindrical surfaces of respective portions 60, 62 of posts 56. In some alternative embodiments, a cylindrical boss or bushing is provided adjacent the openings of the bins 50 coupled to posts 56 to increase the surface area of the rotative bearing interface between bins 50 and posts 56. In other alternative embodiments, the rotative bearing interface is provided by bearings with rolling elements that rotatably couple bins 50 to posts 56.

A bottom wall region around each of the openings in the bottom wall of the lowermost bins 50 coupled to posts 56 abuts an annular surface of respective disks 58, which annular surfaces face upwardly and extend radially outwardly from respective portions 60. Similarly, a bottom wall region around each of the openings in the bottom wall of the uppermost bins 50 coupled to posts 56 abuts an annular surface of respective portions 60, which annular surfaces face upwardly and extend radially outwardly from respective portions 62. Thus, the upwardly facing, annular surfaces of disks 58 prevent the lowermost bins 50 coupled to posts 56 from falling downwardly off of posts 56 and the upwardly facing, annular surfaces of portions 60 prevent the uppermost bins 50 coupled to posts 56 from falling downwardly toward the lowermost bins 50 situated thereunder. In addition, as bins 50 pivot about posts 56, a thrust bearing interface is provided between the respective upwardly facing, annular surfaces of disks 58 and portions 60 of posts 56 and the bottom walls of the associated bins 50. In alternative embodiments, one or more thrust washers, thrust bushings, or thrust bearings with rolling elements are situated between the upwardly facing, annular surfaces of post 56 and the bottom walls of the bins 50 coupled to posts 56.

Support 32 of illustrative cart 14 comprises a pair of spaced-apart, vertical members or posts 64 that extend upwardly from base 18 as shown in FIGS. 2-4. Illustrative posts 64 are cylindrical in shape. Support 32 further comprises a block 66 coupled to a lower portion of posts 64 and a storage box 68 coupled to an upper portion of posts 64. Box 68 has an interior region 69 that is sized to receive therein items such as, for example, clip boards. A lid or door 71 is coupled to a top of box 68 for movement between a closed position blocking access to interior region 69, as shown in FIG. 2, and an opened position allowing access to interior region 71 through the top of box 68, as shown in FIG. 3.

Two bins 50 are coupled to each post 64 for pivoting movement about vertical axes defined by the respective posts 64. Each of the bins 50 coupled to posts 64 is movable independently between a storage position situated underneath the associated tray 52 and a use position situated at least partly out from underneath the associated tray 52 so that items can be placed in or removed from open tops of bins 50. The uppermost bins 50 coupled to posts 64 are supported above the lowermost bins 50 coupled to posts 64 so that the bottom wall of the uppermost bins 50 is vertically spaced apart from the top surface of the respective lowermost bins 50 which lie thereunder.

Bins 50 coupled to posts 64 each include a collar 70 having a bore (not shown) that receives a portion of the respective post 64 therein with a minimal amount of clearance therebetween. Thus, as bins 50 pivot about posts 64, a rotative bearing interface is provided between the surfaces that define the bores of collars 70 and the outer cylindrical surfaces of respective posts 64. In some alternative embodiments, bushings or bearings with rolling elements are provided in the bores or collars 70 to provide the rotative bearing interface between bins 50 and posts 64. In the illustrative embodiment, collars 70 are appended to respective rear vertical walls of bins 50 adjacent the open tops of bins. In alternative embodiments, collars 70 are coupled to other walls of bins, such as the bottom wall or one of the sidewalls, and/or are situated closer to the bottom of bins 50 than the tops of bins 50.

In the illustrative embodiment of FIGS. 2-4, bottom surfaces of collars 70 of the lowermost bins 50 coupled to posts 64 abut the top surface of block 66. Thus, the top surface of block 66 supports the associated bins 50 in spaced relation with base 26 and prevents these bins 50 from moving downwardly on posts 64 toward base 26. In addition, as the lowermost bins 50 coupled to posts 64 pivot about posts 64, a thrust bearing interface is provided between the bottom surfaces of the respective collars 70 and the top surface of block 66. In some alternative embodiments, one or more thrust washers, thrust bushings, or thrust bearings with rolling elements are situated between the collars 70 and block 66 to provide the thrust bearing interface.

This disclosure contemplates several types of thrust bearing interfaces between posts 64 and the collars 70 of the associated uppermost bins 50. In some embodiments, bottom surfaces of collars 70 of the uppermost bins 50 coupled to posts 64 abut respective top surfaces of spacers (not shown) that are situated on posts between the uppermost collars 70 and the lowermost collars 70. In alternative embodiments, posts 64 are formed to include annular, upwardly facing shoulder surfaces on which the bottom surfaces of the uppermost collars 70 rest. In still other embodiments, collars 70 have shoulder surfaces formed in the bores thereof that interface either with surfaces formed in posts 64 or with structures coupled to posts 64 to maintain the vertical position of respective bins 50 on posts 64 and to provide a thrust bearing interface between respective bins 50 and posts 64. In some alternative embodiments, one or more thrust washers, thrust bushings, or thrust bearings with rolling elements are situated between uppermost collars 70 and whatever structure or surface supports the associated bins 50 from moving downwardly relative to posts 64.

Trays 52 are coupled to each post 64 for pivoting movement about the vertical axes defined by the respective posts 64. When cart 14 is docked to device 12, each of the trays 52 coupled to posts 64 is movable independently between a storage position situated underneath platform 22 and a use position situated at least partly out from underneath the platform 22 so that at least some of work surface 54 is exposed for use. Trays 52 are supported on posts 64 so that a slight amount of clearance exists between the bottom surfaces of trays 52 and the top surfaces of each of the upper set of bins 50 that lie thereunder.

Illustratively, each of trays 52 includes a collar 72 that has a bore (not shown) which receives a portion of the respective post 64 therein with a minimal amount of clearance therebetween. Thus, as trays 52 pivot about posts 64, a rotative bearing interface is provided between the surfaces that define the bores of collars 72 and the outer cylindrical surfaces of respective posts 64. In some alternative embodiments, bushings or bearings with rolling elements are provided in the bores of collars 72 to provide the rotative bearing interface between trays 52 and posts 64. Illustratively, collars 72 are each appended to the rear, inboard corner of the main tray portion of the associated tray 52. In alternative embodiments, collars 72 are appended to another part of the main tray portions of trays 52.

This disclosure contemplates several types of thrust bearing interfaces for supporting trays 52 on posts 64. In some embodiments, bottom surfaces of collars 72 abut respective top surfaces of collars 70 of the uppermost bins 50 coupled to posts 64. In such embodiments, collars 72 project by a slight amount below the bottom surfaces of the main portions of respective trays 52 and/or the collars 70 of the uppermost bins 50 coupled to posts 64 project by a slight amount above the top surfaces of the remainder of these bins 50 so that the main tray portions of trays 52 are spaced from the top surfaces of the upper set of bins 50 thereunder. In alternative embodiments, a spacer (not shown) is provided between collars 72 and the collars 70 thereunder. In other alternative embodiments, posts 64 are formed to include annular, upwardly facing shoulder surfaces on which the bottom surfaces of the collars 72 rest. In still other embodiments, collars 72 have shoulder surfaces formed in the bores thereof that interface either with surfaces formed in posts 64 or with structures coupled to posts 64 to maintain the vertical position of trays 52 on posts 64 and to provide a thrust bearing interface between respective trays 52 and posts 64. In further alternative embodiments, one or more thrust washers, thrust bushings, or thrust bearings with rolling elements are situated between collars 72 and whatever structure or surface supports the associated trays 52 from moving downwardly relative to posts 64.

In the illustrative embodiment, as trays 52 pivot about posts 64, posts 56 and the bins 50 coupled thereto move along with trays 52. Thus, when cart 14 is docked to device 12, each of trays 52 may be pivoted out from underneath platform 22 and then each of the bins 50 coupled to posts 56 may be pivoted out from underneath the associated tray 52. Of course, the bins 50 coupled to posts 56 also may be pivoted out from underneath trays 52 while trays 52 remain in their storage positions beneath platform 22. In alternative embodiments, one or more arms or other structural members extend from support 32 in a cantilevered manner beneath bins 50 and, in such embodiments, posts 56 are coupled to distal ends of the members and extend upwardly therefrom to support the associated bins 50. In these alternative embodiments, the bins 50 on posts 56 that extend upwardly from the structural members do not pivot with trays 52 as trays 52 pivot about posts 64.

Referring now to FIGS. 5 and 6, a combination 110 comprises device 12 and a first alternative cart 114. Cart 114 has a base 126, a set of wheels 128 coupled to base 126, a structure 130 for supporting supplies and/or equipment, and a support 132 that supports structure 130 above base 126. Cart 114 also has a portion of a docking mechanism (not shown) that is similar to portion 42 described above in connection with cart 14 and that interfaces with portion 40 mounted to base 18 of device 12 in order to dock cart 114 to device 12. Thus, cart 14 and cart 114 are both dockable to device 12. As was the case with cart 14, cart 114 is releasable from device 12 via a suitable release mechanism. When cart 114 is docked to device 12, a portion of structure 130 of cart 114 is received in space 44 of device 12, a portion of base 126 of cart 114 is received in space 48 beneath base 18 of device 12, and a portion of base 18 of device 12 is received in a space (not shown) defined between structure 130 and base 126 of cart 114. The space between structure 130 and base 126 of cart 114 is similar to space 46 between structure 30 and base 26 of cart 14.

Structure 130 of cart 114 comprises a plurality of containers or bins 150 in which supplies, waste, or equipment may be placed by caregivers, if desired. Unlike bins 50 of cart 14, which illustratively have main container portions of substantially the same size, some of bins 150 are of a different size than others of bins 150. For example, a first pair of bins 151 are deep and have small-size open tops, a second pair of bins 153 are shallow and have large-size open tops, and a third pair of bins 155 are of intermediate depth and have large-size open tops. Structure 130 of cart 114 further comprises a pair of shelves or trays 152, each of which has an upwardly facing work surface 154. When cart 114 is docked to device 12, each of bins 150 and trays 152 are movable between respective storage positions situated in space 44 and respective use positions situated at least partly outside of space 44.

Support 132 of illustrative cart 114 comprises a lower unit 166 coupled to base 126 and a pair of telescopic vertical members or posts 164 that extend upwardly from lower unit 166 as shown in FIGS. 5 and 6 (posts 164 are shown in phantom in FIG. 5). Telescopic posts 164 each include a first member or tube 163 to which respective bins 151, 153, 155 are coupled for pivoting movement about an associated vertical axis 167. Posts 164 also each include a second member or tube 165 that extends and retracts relative to tube 163. Support 132 further comprises a pair of arm assemblies 156, each of which couples a respective a tray 152 to the upper end of an associated tube 165 as shown in FIG. 6. Support 132 also has a push bar 140 coupled to upper ends of tubes 163 by suitable couplers, such as brackets (not shown). Push bar 140 is gripped by caregivers to maneuver cart 114 along floor 34.

Bins 151 each include a collar 170 that couples the main container portion of bins 151 to posts 164. Bins 155 each include a collar 174 and an arm 176 that couples the main container portions of bins 155 to respective posts 164. Similarly, bins 153 each include a collar 178 and an arm 180 that couples the main container portions of bins 153 to respective posts 164. Collars 170, 174, 178 each have a bore that receives therein a respective portion of tube 163 of associated posts 164. A rotative bearing interface is provided between the bores of each of collars 170, 174, 178 and the outer surface of the respective tube 163. Any of the rotative bearing interfaces described above in connection with the coupling of bins 50 and trays 52 of cart 14 to posts 56, 64 may be used in connection with the coupling of bins 150 of cart 114 to post 164.

Collar 170 is situated on post 164 just above lower unit 166, collar 174 is situated on post 164 just above collar 170, and collar 178 is situated on post 164 just above collar 172. A thrust bearing interface is provided between each of collars 170 and unit 166, between each of collars 174 and respective collars 170 thereunder, and between each of collars 178 and respective collars 174 thereunder. Any of the thrust bearing interfaces described above in connection with the coupling of bins 50 and trays 52 of cart 14 to posts 56, 64, including the use of spacers, may be used in connection with the coupling of bins 150 of cart 114 to post 164.

Arms 176 are configured to reach around respective bins 151 to couple to the main container portions of associated bins 155 and arms 180 are configured to reach around respective bins 151 to couple to the main container portions of associated bins 153. In the illustrative embodiment, when all of bins 151, 153, 155 are in the storage positions, bins 151 may be moved to the respective use positions while bins 153, 155 remain in the respective storage positions as shown, for example in FIG. 6 with reference to one of bins 151. During such movement of bins 151 from the respective storage positions to the respective use positions, bins 151 pivot away from arms 176, 180. However, when all of bins 151, 153, 155 are in the storage positions, movement of any of bins 153, 155 toward the respective use position causes the associated bin 151 also to pivot toward its use position due to arms 176, 180 contacting the associated bin 151. Such a situation is shown, for example, in FIG. 5, where one of bins 153 is moved partially out from underneath tray 152 toward its use position, thereby causing the associated bin 151 to be moved partially out from underneath the associated tray 152 toward its use position.

When cart 114 is docked to device 12, trays 152 are movable between respective storage positions situated in space 44 beneath platform 22 and respective use positions situated outside space 44 and alongside platform 22, as mentioned above. Trays 152 are coupled to the upper ends of tubes 165 by arm assemblies 156, as also mentioned above. Each arm assembly 156 has one or more links or arms 158 that supports the associated tray 152 relative to the associated tube 165 as shown in FIG. 6. At least one of arms 158 of each assembly 156 is coupled to the upper end of a respective tube 165 for pivoting movement. Arms 158 are configured to permit trays 156 to move horizontally between the storage position beneath platform 22 and an intermediate position out from underneath platform 22 when cart 114 is docked to device 12.

Support 132 has a pair of lift mechanisms (not shown) that are actuated to extend tubes 165 relative to tubes 163 to lift trays 152 from the respective intermediate positions to the respective use positions. In some embodiments, the lift mechanisms of support 132 comprise gas springs, each of which is coupled to respective tubes 163 and to respective tubes 165. In such embodiments, the gas springs are situated in the interior regions of tubes 163, 165. A pair of foot pedals 160 are coupled to lower unit 166 and each foot pedal is depressed repeatedly through a first stroke length to pump air into the associated gas spring to raise the respective tube 165, assembly 156, and tray 152 from the intermediate position to the use position. When trays 152 are in the use positions, as shown in FIG. 6, work surfaces 154 of trays 152 are substantially coplanar (i.e. within a couple inches) with an upper surface 184 of platform 22 and with an upwardly facing patient-support surface 186 of a mattress 188 carried by platform 22.

When each foot pedal 160 is depressed through a second stroke length, which is longer than the first stroke length, and is held at the bottom of the second stroke length, air escapes from the associated gas spring causing the associated tube 165 to retract relative to tube 163 so that the respective tube 165, assembly 156, and tray 152 move downwardly from the use position to the intermediate position. From the intermediate position, trays 152 may be pushed horizontally into the storage position received in space 44. In other embodiments, lift mechanisms other than gas springs are included in support 132 to change the elevation of trays 152. Such alternative lift mechanisms may include manual clutch and release mechanisms, akin to those used in telescopic microphone stands or IV poles; manual jacking mechanisms, akin to the mechanisms provided in automobile jacks; lead screw mechanisms that are either hand-operated or foot-operated; and any other mechanism capable of raising and lowering trays 152 relative to the rest of cart 114.

Referring now to FIGS. 7 and 8, a combination 210 comprises device 12 and a second alternative cart 214. Cart 214 has a base 226, a set of wheels 228 coupled to base 226, a structure 230 for supporting supplies and/or equipment, and a support 232 that supports structure 230 above base 226. Cart 214 also has a portion of a docking mechanism (not shown) that is similar to portion 42 described above in connection with cart 14 and that interfaces with portion 40 mounted to base 18 of device 12 in order to dock cart 214 to device 12. Thus, carts 14, 114, 214 are each releasably dockable to device 12. As was the case with cart 14 and cart 114, cart 214 is releasable from device 12 via a suitable release mechanism. When cart 214 is docked to device 12, a portion of structure 230 of cart 114 is received in space 44 of device 12, a portion of base 226 of cart 114 is received in space 48 beneath base 18 of device 12, and a portion of base 18 of device 12 is received in a space (not shown) defined between structure 230 and base 226 of cart 114. The space between structure 230 and base 226 of cart 214 is similar to space 46 between structure 30 and base 26 of cart 14.

Structure 230 of cart 214 comprises a container or bin 250 in which supplies, waste, or equipment may be placed by caregivers, if desired. Structure 230 of cart 214 further comprises an equipment-support shelf 252 which has an equipment-support surface 254 as shown best in FIG. 7. When cart 214 is docked to device 12, bin 250 is movable between a storage position situated in space 44 and a use position situated at least partly outside of space 44. Support 232 of illustrative cart 214 comprises a lower unit 266 coupled to base 226 and a pair of vertical members or posts 264 that extend upwardly from lower unit 266 as shown in FIGS. 7 and 8. Support 232 also has a push bar 240 that is coupled to posts 264. Push bar 240 comprises a pair of vertical portions or posts 242 and a U-shaped grip handle portion 244 that interconnects portions 242. Illustrative portion 244 extends generally horizontally from the upper ends of vertical portions 242 and is gripped by a caregiver to maneuver cart 214 along floor 34. Lower ends (not shown) of vertical posts 242 are coupled to the upper ends of posts 264. A central region of portion 244 has a layer of padding 246 thereon to provide caregivers with a comfortable gripping area on portion 244.

Bin 250 includes a collar 270 that couples the main container portion of bin 250 to one of posts 242 of push bar 240 for pivoting movement about a vertical axis 267 defined by the respective post 242 as shown in FIGS. 7 and 8. Collar 270 has a bore that receives therein a portion of the post 242 on which bin 250 is mounted. A rotative bearing interface is provided between the bore of collar 270 and the outer surface of the respective post 242. Any of the rotative bearing interfaces described above in connection with the coupling of bins 50 and trays 52 of cart 14 to posts 56, 64 may be used in connection with the coupling of bin 250 of cart 214 to the respective post 242. Collar 270 is situated on post 242 just above the top surface of post 264. A thrust bearing interface is provided between collar 270 and post 264. Any of the thrust bearing interfaces described above in connection with the coupling of bins 50 and trays 52 of cart 14 to posts 56, 64 may be used in connection with the coupling of bin 250 of cart 214 to the associated post 242.

Shelf 252 extends horizontally from lower unit 266 in a cantilevered manner as shown in FIGS. 7 and 8. Thus, a bottom surface of shelf 252 overlies one or more frame members 227 of base 226 in spaced-apart relation therewith.

Illustrative surface 254 of shelf 252 has a recess 268 formed therein as shown in FIG. 7. Recess 268 is sized and configured to receive therein a portion of a pair of gas tanks 234, along with portions of outlet hardware 235 and pressure gages 236 associated with tanks 234. In the illustrative embodiment, a flat or planar portion of surface 254, which is adjacent to recess 268, supports a power unit 272. In some alternative embodiments, surface 254 of shelf 252 has one or more recesses that are adapted to receive some or all of other types of equipment. In other alternative embodiments, surface 254 of shelf 252 has no recess at all.

When cart 214 is docked to device 12, so that cart 214 and device 12 are transportable together as a unit, gas from gas tanks 234 may be provided through outlet hardware 235 and through hoses or conduits (not shown) to the patient carried by device 12 or to other equipment, such as ventilation equipment, that are transported with device 12. In addition, electrical power from power unit 272 may be provided through appropriate power cords or wires (not shown) to other equipment, such as ventilation equipment, pumps, monitors, computers, and the like, that are transported with device 12.

Cart 214, therefore, is particularly useful with device 12 when a critically underdeveloped infant supported on device 12 is moved from one location in a healthcare facility to another. In particular, when device 12 is positioned in a particular location within the healthcare facility, utilities such as electricity and medical gases (e.g., oxygen) are available via the infrastructure of the facility such as wall mounted electrical receptacles and gas supply lines which are routed from a central location in the building to gas supply receptacles in the care room. To move device 12 from one location to another with the facility, or even to a different facility, device 12 and the equipment associated therewith is disconnected from these utilities. However, such utilities (e.g., electricity, oxygen, and other medical gases) are provided by equipment carried on cart 214. As such, electrical power and medical gases are supplied from the equipment on cart 214 to device 12 and to other equipment associated therewith during transport thereof.

Referring now to FIGS. 9 and 10, a combination 310 comprises device 12 and a third alternative cart 314. Cart 314 has a frame 316 and a structure or storage module 330 for supporting supplies and/or equipment. Storage module 330 is carried by frame 316, as shown in FIG. 9, and is transferable from frame 316 to device 12 to be carried in space 44 of device 12, as shown in FIG. 10. Frame 316 has a base 326, four wheels 328 coupled to base 326, and a support 332 that supports structure 330 above base 326 when structure 330 is coupled to frame 316. Base 326 has a transversely extending, horizontal frame member 318 to which two of wheels 328 are coupled and a pair of spaced-apart, longitudinally extending, horizontal frame members 320 to which the other two wheels 328 are coupled.

A suitable coupling mechanism is provided for detachably coupling module 330 to frame 316. Such a coupling mechanism may have, for example, a connector and a receiver similar to connector 40 and receiver 42 described above in connection with docking mechanism 16. In addition, a suitable release mechanism is provide to uncouple the connector and receiver so that module 330 is separable from frame 316.

Unlike carts 14, 114, 214, cart 314 does not have a portion of docking mechanism 16 that interfaces with portion 40 mounted to base 18 of device 12 in space 48 beneath base 18, but rather, module 330 has a portion of a docking or coupling mechanism (not shown) that interfaces with another portion of the coupling mechanism mounted to device 12 in space 44. In some embodiments, the portion of the coupling mechanism mounted to device 12 extends from the top of base 18. In such embodiments, the portion of the coupling mechanism extending from the top of base 18 is mounted to base frame 36 and projects upwardly through an aperture or slot formed in shroud 38. Also in these embodiments, the portion of the coupling mechanism mounted to module 330 is mounted near a bottom corner region of module 330 (i.e. the bottom corner of module 330 nearest support 24 of device 12 when module 330 is coupled to device 12).

In some embodiments, the coupling mechanism of combination 310 that couples module 330 to device 12 includes a first portion or connector and a second portion or receiver, similar to connector 40 and receiver 42 described above in connection with combination 10. A suitable release mechanism (not shown), such as a hand-operated release mechanism or a foot-operated release mechanism, is provided on either module 330 or device 12 to release the coupling mechanism to permit module 330 to be transferred from device 312 back onto frame 316 of cart 314. Thus, combination 310 has a first coupling mechanism for releasably coupling module 330 to frame 316 and a second coupling mechanism for releasably coupling module 330 to device 12.

During the process of transferring module 330 to device 12 from frame 316, cart 314 is moved into a "docked" position having module 330 of cart 314 received in space 44 of device 12, having a portion of base 326 of cart 314 received in space 48 beneath base 18 of device 12, and having a portion of base 18 of device 12 received in a space 346 defined between module 330 and base 326 of cart 314. As cart 314 moves into the docked position, the first and second portions of the second coupling mechanism, which couples module 330 to device 12, lock together. Base 326 interacts with base 18 to properly orient cart 314 relative to device 12 during movement of cart 314 toward the docked position so that the first and second portions of the second coupling mechanism are properly aligned prior to docking.

If the first and second portions of the first coupling mechanism, which couples module 330 to frame 316, remain locked together while the first and second portions of the second coupling mechanism are locked together, then cart 314 and device 12 are transportable together as a unit. However, more often than not, after the first and second portions of the second coupling mechanism lock together, the release mechanism associated with the first coupling mechanism is operated to release module 330 from frame 316, and then, frame 316 is pulled away from device 12 leaving module 330 coupled to device 12 to be transported therewith.

During the process of transferring module 330 from device 12 back to cart 316, frame 316 is moved back into the docked position so that the first and second portions of the first coupling mechanism lock together so that module 330 is once again coupled to frame 316. Thereafter, the release mechanism associated with the second coupling mechanism is operated to release module 330 from device 12, and then, cart 314 is pulled away from device 12 having module 330 being carried by frame 316. In some embodiments, the release mechanism associated with the first coupling mechanism is configured to automatically release the first coupling mechanism when the first and second portions of the second coupling mechanism lock together and the release mechanism associated with second coupling mechanism is configured to automatically release the second coupling mechanism when the first and second portions of the first coupling assembly lock together. In such embodiments, module 330 does not lock to frame 316 and to device 12 simultaneously, but rather is locked only to one or the other of frame 316 and device 12 at any particular instance in time.

Module 330 comprises a main housing 334, a pair of upper drawers 336, a pair of lower drawers 338, and a pair of bins or containers 350 as shown in FIGS. 9 and 10, although only one each of drawers 336, 338 can be seen in the Figs. Drawers 336, 338 and bins 350 are coupled to housing 334 for movement between respective closed positions and respective opened positions. In the opened positions, items can be placed into or removed from the open tops of drawers 336, 338 and bins 350 as desired. In some embodiments, bins 350 are used as trash receptacles. A recess 348 is formed in each side wall of housing 334. A cross bar 349 is appended to each side wall of housing 334 and extends horizontally across an associated recess 348. Recesses 348 are sized so that clipboards 349 may be placed in recesses 348 behind bars 349. Bars 349 prevent the clipboards 349 from falling out of recesses 348.

Drawers 336, 338 are situated at the sides of module 330 and move generally horizontally relative to housing 334 when moving between the opened and closed positions. Each upper drawer 336 is located above an associated lower drawer 338. Illustrative drawers 336, 338 are all approximately the same size. In alternative embodiments, drawers of various sizes are included in module 330. Drawers 336, 338 each have a transparent front panel 337 which permits caregivers to view the contents of drawers 336, 338. For example, a set of folded blankets 339 are stored in one of upper drawers 336. In alternative embodiments, the front panels of the drawers included in module 330 are not transparent. Drawers 336, 338 also each have a handle 342 that is grasped by caregivers, if desired, while moving drawers 336, 338 between the opened and closed positions.

Bins 350 are arranged in side-by-side relation at the end of housing 334 which is accessible when module 330 is coupled to device 12. When moving between the opened and closed positions, bins 350 pivot about an axis (not shown) that extends through lower corner regions of bins 350. When pivoted to the opened positions, open tops of bins 350 are accessible for placement of items into bins 350 or removal of items from bins 350. Bins 350 each include a handle 344 that is grasped by caregivers, if desired, while moving bins 350 between the opened and closed positions.

Module 330 further has a pair of shelves or trays 352 coupled to the top of housing 334, one of trays 352 being situated just above the other of trays 352 when both trays are in a respective storage position above housing 334 as shown in FIG. 9. Each of trays 352 has an upwardly facing work surface 354. Suitable mechanisms, such as slide mechanisms and/or pivot mechanisms, couple each of trays 352 to housing 334 and permit trays 352 to move from the respective storage positions to respective use positions. A pair of grips 353 are mounted to two of the corner regions of the bottom tray 352 to facilitate movement of the bottom tray 352 beneath the top tray 352 between the storage position and the use position. When module 330 is coupled to device 12, one of trays 352 may be moved to its use position out from underneath platform 22 on one side of device 12 and the other of trays 352 may be moved to its use position out from underneath platform 22 on the other side of device 12. In the illustrative embodiment, the bottom tray 352 is able to move out from underneath platform 22 in a multitude of directions as shown, for example, in FIG. 10 where the bottom tray 352 is shown moved to a position extending partially outwardly from the side of platform 22 and partially outwardly from the end of platform 22. Thus, the bottom tray 352 has a multitude of use positions. In some embodiments, the top tray 352 also has a multitude of use positions.

Support 332 of illustrative frame 316 comprises a pair of vertical frame members or posts 364 that extend upwardly from frame member 318 of base 326 as shown in FIG. 9. Support 332 also has a push bar 340 that is coupled to upper ends of posts 364 by brackets 368. Push bar 340 is slightly arcuate or curved and is gripped by a caregiver to maneuver cart 314 along floor 34. Illustrative support 332 further comprises a pair of posts 366 that extend horizontally from the upper ends of posts 364 in a cantilevered manner. Posts 366 are received in post-receiving bores formed in housing 334 of module 330 to support module 330 above frame members 320 of base 326 in spaced-apart relation therewith. Thus, in the illustrative embodiment, posts 366 serve as a connector of the coupling mechanism that couples module 330 to frame 316 and the post-receiving bores formed in housing 334 serve as a receiver of the coupling mechanism that couples module 330 to frame 316. In some embodiments, additional coupling elements are provided to releasably lock housing 334 onto posts 366.

In the illustrative combinations 10, 110, 210, 310, device 12 is an infant thermal support device that supports premature infants. It is desirable to minimize the amount of noise and activity to which a premature infant is exposed in order to facilitate the development of the premature infant. Thus, it is contemplated by this disclosure that carts 14, 114, 214, 314 are transported separately from device 12 to one or more areas in a healthcare facility to be loaded with supplies and/or equipment and then transported back to device 12 for docking therewith. Thus, the infant is not exposed to the noise and activity associated with loading supplies and/or equipment onto carts 14, 114, 214, 314. Of course, supplies and/or equipment may also be loaded onto carts 14, 114, 214, 314 when carts 14, 114, 214, 314 are docked to device 12.

Each of carts 14, 114, 214, 314 may be loaded with different types of supplies and equipment that are associated with different types of medical treatments for the infant or that are associated with different stages of development or medical condition of the infant. Carts 14, 114, 214, 314 may then be interchangeably docked to device 12, as desired, to provide infant care stations of various configurations. Thus, the contents of the carts 14, 114, 214, 314 may be customized to perform a particular function or to have particular resources. In addition, the bins and drawers of carts 14, 114, 214, 314 may be equipped with locks or other types of security devices to prevent unauthorized access to the contents stored in the respective bins or drawers. Such locks or security devices may be used when drugs or medicines are stored in any of carts 14, 114, 214, 314.

As previously mentioned, illustrative device 12 is an infant thermal support device. In some embodiments, device 12 is of the type shown and described in the following U.S. patents and patent applications, each of which is hereby incorporated by reference herein: U.S. Pat. Nos. 5,453,077; 5,817,002; 5,817,003; 5,759,149; 5,971,913; 5,971,914; 6,022,310; 6,024,694; 6,036,634; 6,049,924; 6,071,228; 6,270,452; 6,296,606; 6,345,402; Ser. No. 09/688,528 filed on Oct. 16, 2000; Ser. No. 09/571,449 filed on May 16, 2000; Ser. No. 09/838,789 filed on Apr. 20, 2001; and Ser. No. 10/027,496 filed on Dec. 21, 2001.

Illustrative device 12 has an infant enclosure 74 above platform 22 as shown in FIGS. 2-6, 8, and 10. Enclosure 74 comprises a pair of transparent side walls or panels 76, a pair of end walls or panels 78, and a canopy 80. Enclosure 74 defines an infant compartment above platform 22. One or more of walls 76, 78 are movable between raised positions extending upwardly from platform 22 and lowered positions adjacent the associated side or end of platform 22. In some embodiments, access ports and/or line pass-through ports are formed in one or more of walls 76, 78. In such embodiments, appropriate covers or doors are typically provided for opening and closing the ports in walls 76, 78. Canopy 80 comprises a pair of canopy halves 82 and device 12 has an overhead arm 84 to which canopy halves 82 couple. Canopy halves 82 are hinged to arm 84 for movement between lowered positions extending downwardly from arm 84 and raised positions extending upwardly from arm 84.

Device 12 has a telescopic, vertical arm assembly 86 that couples arm 84 to platform 22. A drive mechanism (not shown), such an electric linear actuator, operates to extend and retract arm assembly 86, thereby to raise and lower, respectively, arm 84 and canopy 80 relative to platform 22 between raised and lowered positions. When panels 76, 78 are in their raised positions and when assembly 86 and canopy halves 82 are in their lowered positions, the bottom edges of canopy halves 82 abut or are in close proximity to the upper edges of panels 76, 78 to completely enclose the infant compartment defined by enclosure 74.

Support 24 of device 12 is telescopic and has a first member or tube 23 coupled to base 18 and a second member or tube 25 coupled to platform 22 as shown in FIG. 2. Device 12 has a suitable drive mechanism (not shown), such as an electric linear actuator, that operates to extend and retract tube 25 relative to tube 23, thereby to raise and lower platform 22 relative to base 18. Device 12 is configured so that when platform 22 is supported by support 24 in a lowermost position, each of carts 14, 114, 214, 314 (or portions thereof), is able to dock to device 12 without interference from platform 22.

Platform 22 carries convective heating equipment (not shown) and humidification equipment (not shown) that operates to convectively heat and/or humidify the infant compartment. Arm 84 carries a radiant heater (not shown) that operates to direct radiant heat toward platform 22 and the infant carried thereon. A control system is housed in platform 22 and/or in arm 84 to command the operation of the convection heating equipment, the humidification equipment, the radiant heater, the drive mechanism for raising and lowering arm 84, the drive mechanism for raising and lowering platform 22, and other functions of device 12. Illustrative device 12 has a computer 88 carried by an articulated arm assembly 90 that swivels about a segment of vertical arm assembly 86. Computer 88 serves as a user input device to control the operation of the various systems of device 12. Additional details of computer 88 and arm assembly 90 are shown and described in U.S. patent application Ser. No. 10/146,076 which was filed May 15, 2002 and which is hereby incorporated by reference herein.

In some embodiments, computer 88 of device 12 is configured for equipment and supply management. Thus, as equipment and supplies are added to or removed from carts 14, 114, 214, 314, appropriate information regarding the addition or removal of the equipment and supplies may be input into computer 88. It is contemplated by this disclosure that computer 88 is coupled to a computer network of the healthcare facility. Thus, supply and equipment data is communicated between computer 88 and other locations in the healthcare facility. For example, if equipment carried by device 12 or carts 14, 114, 214, 314 malfunctions, computer 88 may be used to communicate an appropriate message via the facility network to maintenance personnel. In addition, if data input into computer 88 indicates that certain supplies carried by the particular cart 14, 114, 214, 314 docked to device 12 have been depleted down to a predetermined threshold level, then an appropriate message may be communicated from computer 88 via the network to notify caregivers to restock the needed supplies.

Although illustrative device 12 is an infant thermal support device capable of heating an infant with convective heat and/or radiant heat, it is contemplated by this disclosure that carts 14, 114, 214, 314 may be used with other patient-support devices, such as, for example, hospital beds, stretchers, infant warmers, infant incubators, and the like, that are appropriately configured to have carts 14, 114, 214, 314 (or portions thereof), docked thereto. Thus, the term "patient-support device" as used in this disclosure, including in the claims, is intended to cover all of these types of device and the equivalents thereof, unless specifically stated otherwise in a particular instance.

Although the invention have been described in detail with reference to certain illustrative embodiments, variations and modifications exist with the scope and spirit of this disclosure as described and defined in the following claims.

The invention claimed is:

1. A combination comprising a patient-support device having a surface on which a patient rests, the patient-support device having a cart-receiving space, and a cart dockable to the patient-support device, the cart having a post and a container coupled to the post, and when the cart is docked to the patient-support device the container is movable about the post between a first position in which at least a portion of the container is situated in the cart-receiving space and a second position in which at least a majority of the container is situated outside the cart-receiving space, wherein the patient-support device comprises an infant thermal support device having a patient-support platform and an infant enclosure carried by the patient-support platform, an infant space being defined between the patient-support platform and the infant enclosure, the patient-support platform carries heating equipment that is operable to heat the infant space, and the cart-receiving space is defined beneath the patient-support platform.

2. The combination of claim 1, wherein the post has a vertical orientation.

3. The combination of claim 1, wherein the container comprises a collar coupled to the post and a main container portion coupled to the collar.

4. The combination of claim 3, wherein the collar has a bore that receives a portion of the post and a rotative bearing interface is provided between the bore and the post.

5. The combination of claim 1, wherein the cart includes a tray coupled to the post for pivoting movement.

6. The combination of claim 5, wherein the tray is situated above the container.

7. The combination of claim 6, wherein the container has a lower collar, the tray has an upper collar, and a thrust bearing interface is provided between the upper and lower collars.

8. The combination of claim 1, wherein the post is situated outside the cart-receiving space when the cart is docked to the patient-support device.

9. The combination of claim 1, wherein the cart further comprises a first base and a first set of wheels coupled to the first base, the post extends upwardly from the first base, and the container is supported by the post above the first base and in spaced-apart relation with the first base.

10. The combination of claim 1, wherein the infant enclosure comprises a set of walls extending upwardly from the patient-support platform and a canopy that is situated atop the set of walls to form the infant enclosure.

11. The combination of claim 1, wherein the cart includes a tray that is movable between a storage position beneath the patient-support platform and a use position alongside the patient-support platform.

12. The combination of claim 1, wherein the cart includes a shelf having an equipment-support surface beneath the container.

13. The combination of claim 12, wherein the equipment-support surface is formed to include a recess adapted to receive at least a portion of a piece of equipment therein.

14. A cart comprising a base, a plurality of wheels coupled to the base, a post extending upwardly from the base, a plurality of storage bins, each storage bin having a main container portion and a coupler extending from the main container portion to couple the respective storage bin to the post for pivoting movement about the post, a tray and an arm assembly, the post comprising a first member and second member that is extendable and retractable relative to the first member, and the arm assembly coupling the tray to the second member.

15. The cart of claim 14, wherein the coupler of each storage bin comprises a collar having a bore that receives a portion of the post therein.

16. The cart of claim 15, further comprising a block coupled to the post, the block having a top surface, and the collar of one of the bins having a bottom surface that abuts the top surface of the block.

17. The cart of claim 14, further comprising a box mounted to the post above the plurality of storage bins and the box has an interior region.

18. The cart of claim 14, wherein the post extends vertically upwardly from the base.

19. The cart of claim 14, further comprising a rotative bearing interface between each of the plurality of storage bins and the post.

20. The cart of claim 14, further comprising a thrust bearing interface between each of the plurality of storage bins and the post.

21. The cart of claim 14, the tray being coupled to the post for pivoting movement.

22. The cart of claim 14, wherein the tray is situated above the plurality of storage bins.

23. The cart of claim 14, further comprising a foot pedal that is depressed to extend and refract the second member of the post relative to the first member to raise and lower, respectively, the tray relative to the base.

24. The cart of claim 14, wherein the arm assembly is configured to permit repositioning of the tray relative to the post.

25. A combination comprising a patient-support device having a surface on which a patient rests, the patient-support device having a cart-receiving space, and a cart dockable to the patient-support device, the cart having a post and a container coupled to the post, and when the cart is docked to the patient-support device the container is movable about the post between a first position in which at least a portion of the container is situated in the cart-receiving space and a second position in which at least a majority of the container is situated outside the cart-receiving space, wherein the cart further comprises a first base and a first set of wheels coupled to the first base, the post extends upwardly from the first base, and the container is supported by the post above the first base and in spaced-apart relation with the first base, and wherein the patient-support device comprises a second base and a second set of wheels coupled to the second base, a lower space is defined beneath the second base, and at least a portion of the first base is situated in the lower space when the cart is docked to the patient-support device.

26. The combination of claim 25, further comprising a docking mechanism having a first portion coupled to the first base and a second portion coupled to the second base, the first portion interfaces with the second portion to dock the cart to the patient-support device, and the first and second portions are situated beneath the second base when the cart is docked to the patient-support device.

27. The combination of claim 25, wherein at least a portion of the second base is situated between the first base and the container when the cart is docked to the patient-support device.

28. A cart comprising a base, a plurality of wheels coupled to the base, a post extending upwardly from the base, a plurality of storage bins, each storage bin having a main container portion and a coupler extending from the main container portion to couple the respective storage bin to the post for pivoting movement about the post, further comprising a tray coupled to the post for pivoting movement, an additional post coupled to the tray, and a plurality of additional storage bins coupled to the additional post for pivoting movement.

29. The cart of claim 28, wherein the tray is situated above the plurality of storage bins.

* * * * *